United States Patent [19]

Meek

[11] 4,336,709
[45] Jun. 29, 1982

[54] RETRIEVAL OF ARTICLES FROM BENEATH THE SURFACE OF A BODY OF WATER

[75] Inventor: Robert P. Meek, Santa Barbara, Calif.

[73] Assignee: Ecomar, Inc., Goleta, Calif.

[21] Appl. No.: 208,266

[22] Filed: Nov. 19, 1980

Related U.S. Application Data

[63] Continuation of Ser. No. 29,450, Apr. 12, 1979, abandoned.

[51] Int. Cl.³ .............................................. G01N 1/04
[52] U.S. Cl. .................................. 73/61.2; 73/170 A
[58] Field of Search ................. 73/425.4, 61.2, 170 A; 9/8 R; 335/285, 286, 305; 294/65.5

[56] References Cited

U.S. PATENT DOCUMENTS

| | | | |
|---|---|---|---|
| 1,200,404 | 10/1916 | White | 294/65.5 |
| 3,189,922 | 6/1965 | Margot | 9/8 R |
| 3,242,740 | 3/1966 | Niskin | 73/425.4 R |
| 3,256,539 | 6/1966 | Clark | 9/8 R |
| 3,367,190 | 2/1968 | Bieri | 73/425.4 R |
| 3,374,494 | 3/1968 | Hunley | 9/8 R |
| 3,512,493 | 5/1970 | Hallanger | 9/8 R |
| 3,715,913 | 2/1973 | Anderson | 73/425.4 R |
| 3,793,889 | 2/1974 | Niskin | 73/425.4 R |
| 3,815,422 | 6/1974 | Niskin | 73/425.4 R |
| 3,952,349 | 4/1976 | Erath | 73/170 A |

Primary Examiner—Kyle L. Howell
Assistant Examiner—Denis E. Corr
Attorney, Agent, or Firm—Donald D. Mon

[57] ABSTRACT

Equipment for raising to the surface of a body of water a retrievable article. A cable extends downwardly, and the article is held to the cable at a selected depth. A buoyancy device with a floodable cavity and a gas supply tank travels down the cable to the article where it magnetically attaches to it, and releases gas to blow the cavity, providing positive lift to the surface for the combination. The retrievable article may be a sediment collector whose apertures are closed by the buoyancy device.

6 Claims, 5 Drawing Figures

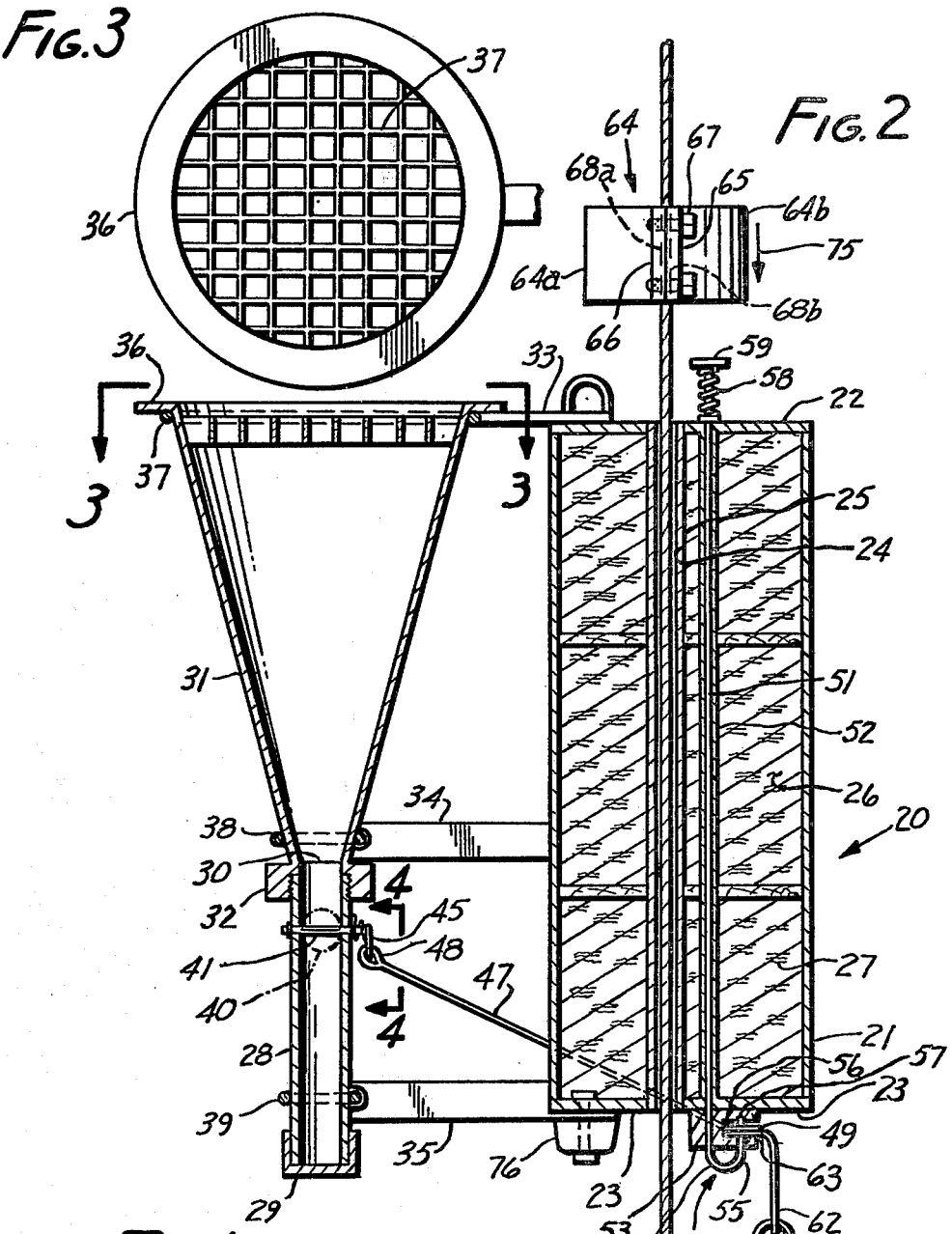
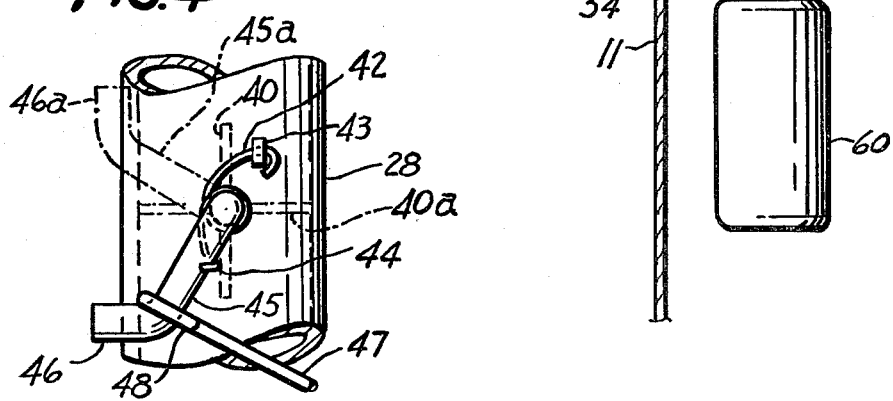

RETRIEVAL OF ARTICLES FROM BENEATH THE SURFACE OF A BODY OF WATER

CROSS-REFERENCE TO OTHER APPLICATION

This is a continuation of applicant's co-pending U.S. patent application, Ser. No. 029,450, filed Apr. 12, 1979, now abandoned.

This invention relates to retrieval of articles from beneath the surface of a body of water.

This invention provides means to raise retrievable articles. One example of such a retrievable article is a sediment collector in which sediment suspended in the water is collected.

There are instances where it is desirable to collect samples of sediment existing in a body of water such as a sea or ocean which sometimes contains substantial amounts of sediment. Such sediment can be caused, for example by dredging operations, off-shore-oil well drilling processes, natural erosion and river runoff or the like. It is commonly desired to ascertain during or after such events how much sediment drops to the bottom.

In places where the water is relatively shallow, the collection of samples of sediment is relatively easy. Where, however the water is relatively deep as is often the case in off-shore drilling operations or discharges from drill ships it is more difficult to collect sediment samples at the greater depths which are involved. A reason for the difficulty resides in the fact that the depth limit to which divers can descend in the water, and the time available for them to dive to recover samples, are limited.

According to the present invention, relatively simple and inexpensive equipment is provided with the use of which sediment samples can be obtained at depths greater than those to which divers can conveniently descend, while using only simple equipment, and using procedures which are simple and quickly accomplished.

The invention is carried out by means of an anchored span of cable long enough to reach from the bottom to a depth near the surface of the water. The cable is held upright by a buoy which is ordinarily attached to the upper end of the cable somewhat below the water surface. A receptacle is provided which in its preferred form is slidable on the cable and has a container with a closed bottom and peripheral sidewall and an open upper mouth with valve means, preferably a pivoted plate, in the mouth. The combination of the receptacle and guide means holding it to the cable has negative buoyancy, and means is provided to return the combination to a lesser depth. Such means may comprise a line, or buoyancy means which can provide sufficient positive buoyancy (lift) as when attached to the combination, will lift it to the lesser depth.

According to feature of the invention, the buoyancy means is inherently negatively buoyant, but provided with means to change its buoyancy to positive, preferably by blowing water out of a shell with a compressed gas.

The above and other features of this invention will be fully understood from the following detailed description and the accompanying drawings, in which:

FIG. 2 is a view, partially in cross-section, of part of the equipment of FIG. 1;

FIG. 3 is a top view of a cover on the collecting funnel of the sediment-collecting receptacle shown in FIGS. 1 and 2;

FIG. 4 illustrates a detail partially in cross-section showing the arrangement of the spring-loaded valve for the sediment collector illustrated in FIGS. 1 and 2.

Figure 1:
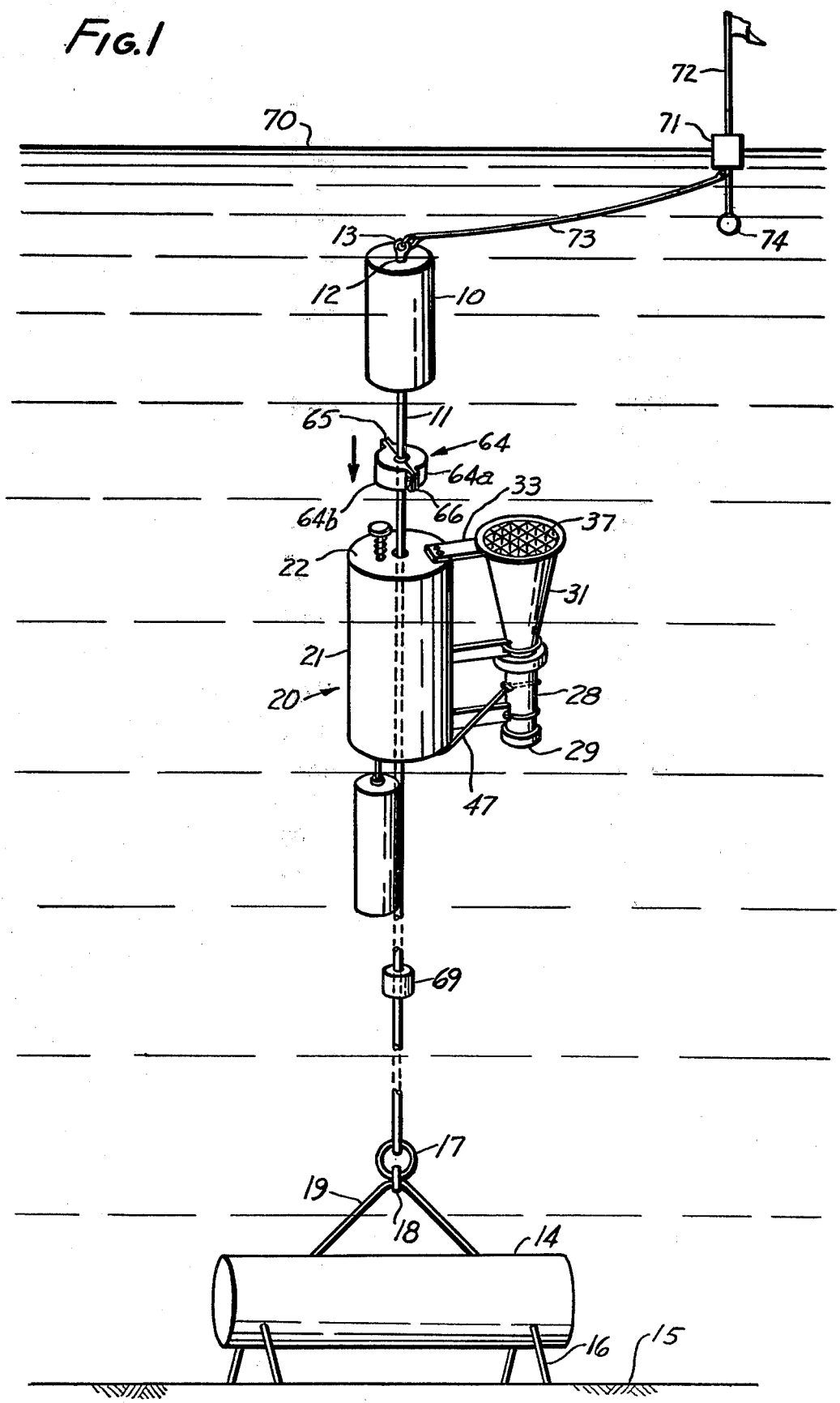
FIG. 1 illustrates one embodiment of equipment for collecting sediment according to this invention.

Referring to FIG. 1 of the drawings there is shown a system for collecting sediment suspended in a body of water. The system comprises a buoy 10 to which there is attached a span of cable 11. The buoy may conveniently be of a cylindrical form and constructed so that it will be buoyant in the water and tend to rise to the surface. In the arrangement illustrated, the buoy is provided with a central hole 12 through it into the upper end of which there is inserted an eyelet 13 the lower end of which is attached to the cable in the region of the buoy. The cable span 11 extends substantially vertically downward to an anchor 14 constructed so that it rests firmly on the bottom 15 of the body of water. The body of the anchor may conveniently be in the form of a cylindrical block of concrete or the like as shown, provided with legs 16 which dig into the bed of the bottom 15. The lower end of cable 11 is attached to a ring 17 secured by a link 18 to a bent rod 19 whose ends are embedded in the anchor body 14.

A floatable body (sometimes called "buoyancy means") in the form of a tube 20 shown in detail in FIG. 2 is mounted to the cable span 11 so that it is free to slide up or down along the cable. This floatable body, whose buoyancy is inherently positive, is in the form of a cylinder 21 having a circular cover 22 at its top end and another circular cover 23 at its bottom end. A hole 24 formed by a cylindrical tube 25 extends along the vertical axis of cylinder 21, the diameter of the tube being sufficient to freely accommodate the cable span 11 which passes through it. The cylindrical walls of cylinder 21 and tube 24 together with the top and bottom members 22 and 23 provide a water-tight annular region 26 which may conveniently be filled with foam.

A sediment collection receptacle or tube 28 closed at its bottom 29 is open at its top 30 where it receives a collection funnel 31 which is threaded to the top of the collection tube by a threaded flange 32 at the lower end of the funnel. The longitudinal axis of the collection tube and the funnel extends vertically and parallel with the cable 11 which is on the longitudinal axis of the flotation tube 20. The collection tube and funnel are attached in this position to the flotation tube 20 by use of brackets 33, 34 and 35 which extend laterally from the flotation tube to the collection tube and funnel alongside the flotation tube. The funnel is conical with its greater diameter at its circular top which is provided with an annular circumferential ring 36 within which is a grill 37 providing baffles with spaces between them through which sediment may fall without permitting the entrance of undesired larger objects such as debris and reduce the potential for resuspension of material once inside the funnel. The annular ring 36 is formed by flaring the funnel material outwardly from the upper conical side of the funnel. The ring 36 is supported on a support ring 37a attached to the bracket 34. The lower end of the funnel is contained within a ring 38 attached to bracket 34. The collection tube 28 is held within a stretchable bungee cord 39 attached to bracket 35. The brackets and the tubular guide through tube 20 are sometimes referred to as "guide means." The combination of the guide means and the receptacle is inherently negatively buoyant.

A spring-loaded butterfly valve 40 in the form of a circular disc positioned within the upper end of the collection tube 28 is mounted on a rotatable spindle 41 extending transversely across the collection tube. This is loaded by a spring 42 one end of which is held in a bracket 43 attached to the exterior wall of the collection tube. The spring encircles the spindle 41 outside the collection tube and its other end 44 bears against a bell crank 45 attached to the spindle, as best seen in FIG. 4. The loading of the spring is such that it tends to maintain the bell crank in its position (broken line) with the butterfly valve disc in its closed position 40a, shown in FIG. 4, wherein the valve lies in a horizontal plane closing the mouth of the collection tube 28. Provision is made, however, for pulling the bell crank downward to the position 45 shown in full-line to hold the butterfly valve in its open position 40 wherein the disc is in a vertical plane as illustrated in FIG. 2. This is done by means of a trip line 47 having a loop 48 at one end and another loop 49 at the other end. The bent end 46 of the bell crank 45 is passed through loop 48 as best seen in FIG. 4. The other loop 49 is held by a trip device 50 mounted on the flotation tube, when it is desired to set the system for the collection of sediment.

This trip device comprises a rod 51 which passes vertically through a tube 52 extending through the flotation tube from top to bottom so that the rod protrudes above the upper cover 22 and below the lower cover 23 of the flotation tube. The lower end of the rod passes through a block 53 fixed beneath the bottom cover 23, below which the rod is bent in the form of a U 54 to provide a vertically extending hook 55 which re-enters the block and passes upwardly across a slot 56 formed at a side of the block so that the end 57 of the rod enters the upper part of the block above the slot. The rod is normally held in this position by a compression spring 58 compressed between the top cover 22 of the flotation body 20 and a cap 59 fixed to the upper end of the rod. By pushing downward on cap 59 against the force of spring 58, the rod can be moved downward far enough so that the upper end 57 of the hook is brought below the slot 56. When the loop 49 is placed within the slot while the rod is thus depressed, this loop will be held by the hook 55 of the rod after pressure on cap 59 is released. The length of the trip line 47 is such that this line, when held at the hook, is taut and pulls the bell crank 45 downward to its position at which butterfly disc 40 lies in the vertical plane, in which it can admit sediment into the sediment collection tube.

There is also provided a drop weight 60 (sometimes called "ballast means"). It is inherently negatively buoyant, and heavy enough to cause the combination of the floatable body, receptacle and guide means to be negative, but when it is dropped, the said combination becomes positively buoyant. Weight 60 has an attaching ring 61 to which there is attached a tether such as a line 62 having a loop 63 at its free end. At the same time that loop 49 is being inserted within the slot 56 as described above, the loop 63 will also be inserted in the slot so that when downward pressure on cap 59 of rod 50 is released after having been applied, the loop 63 will also be held in the slot by the upstanding hook 55 of the rod.

For the purpose of tripping the rod 51 to release the loops 49 and 63 after they have been attached in the slot as described above, there is provided a trip weight 64 loosely surrounding cable span 11 between buoy 10 and the flotation tube 20. This trip weight is made in two parts 64a and 64b adapted to be fitted together around the cable. Each part 64a and 64b has a pair of flanges 65 and 66 diagonally opposite each other and extending laterally outward with respect to the body of the trip weight. The mating flanges of the respective parts 64a and 64b are attached to each other by bolts 67 by threading each bolt into a threaded hole through the mating flange. Along the vertical center line of the joined parts 64a and 64b there is formed a half-cylinder in each part such that when the two parts are bolted together the half-cylinders 68a and 68b together form a complete cylindrical hole along the central axis, of the proper diameter to permit the cable 11 to pass through. If it is desired to leave this weight in place, and merely require its release at the time of recovery of the receptacle, this hole will be dimensioned relative to the diameter of the cable so that when the bolts 67 are completely tightened, the two parts 68a and 68b firmly grip the cable so that the trip-weight becomes fixed to the cable. Thus, the trip weight can be fixed at any elevation along the cable where it is desired to tighten the bolts. When, however, the bolts are loosened, this gripping to the cable is released so that the trip-weight falls of its own weight. If the weight is to be applied by the diver at the time of recovery, then the hole may be larger, and no retention means need be provided.

In any body of water where the equipment is set up to collect sediment samples, the length of the cable span 11 will ordinarily be selected so that the buoy 10 remains somewhat beneath the surface 70 of the water in order that the cable will always be held by the buoy in a vertical position, as illustrated in FIG. 1, in spite of a rise or fall of the water level due to changing tides or other conditions which may change the level. Since the buoy is ordinarily beneath the water, it will usually be desired to provide a surface marker to indicate its location which may be done by a surface buoy 71 carrying a flag 72 or the like which extends above the water surface, this surface buoy being attached to the buoy 10 by a suitable tether 73. A counterbalance weight 74 extending downward from the surface buoy 71 will serve to maintain the flag in an upright position.

Another feature which will usually be desirable is the provision of a zinc anode 76 fixed in contact with the metal part of the equipment to prevent or minimize deterioration due to galvanic action.

From the foregoing description of the equipment it will become apparent how the device of FIG. 1 is operated to collect sediment. The equipment will be taken by boat or helicopter to the desired location in the body of water to be sampled and after attaching the end of the cable 11 to the anchor 14 with a stop 69 fixed to the cable at the desired distance above the anchor, for example, thirty feet more or less, the flotation tube 20 with the sediment tube and its funnel attached, will be placed on the cable above the stop 69, and the upper end of the cable span 11 will be attached to the buoy 10 as described. The tether 73 with the signal float 71 will also be attached to the buoy. If desired, the trip-weight 64 will be attached to the cable span 11 at a position somewhat below the buoy 10 and tightened to fix it to the cable. After attaching the tethers 47 and 62 to the hook 55 as described above, the equipment thus assembled will be lowered into the water so that the anchor rests on the bottom and the cable 11 stands up vertically and taut enough so that it does not sag, as it is held in that position by the buoy 10 which will be somewhat below the surface of the body of water, while the signal flag on its float 71 will be plainly visible from above the water.

Due to the attachment of drop-weight 60 the flotation tube with the sediment collector attached will drop down along the cable until the bottom of the flotation tube rests on the stop 69. The butterfly valve will be held open by the taut trip-wire 47 in the position illustrated in FIG. 2 so that sediment present in the body of water above the collection funnel 31 will drop into the collection tube. Sediment will be collected in this manner for an established period of time at the end of which time period the bolts 67 will be loosened at the trip-weight, ordinarily by a diver, (or instead a loose weight can be placed around the cable at that time) so that the trip-weight will fall, as indicated by arrow 75 in FIG. 2, with enough force on the cap 59 of the trip rod 51 to push the rod downward enough so that the upstanding hook 55 is brought below the slot 56 to release both the trip wire 47 and the tether 62. This action will cause the spring 42 to turn the butterfly valve disc to its closed horizontal position so that no more sediment can enter the collection tube. At the same time the drop weight 60 will be released and sacrificed. It will fall to the bottom. With the drop weight (ballast) removed, the positive buoyance of the flotation tube 20 is sufficient to carry the trip-weight, the receptacle and the guide means (in other words everything except the ballast and stop 69) to a lesser depth at the buoy. Since the flotation device and collection tube will now be only a relatively short distance below the water surface they can easily be reached by a freely swimming diver who will then detach the collection tube from the funnel 31 at the screw threads. The collection tube can then be removed and carried to the surface by the diver for analysis of its contents, a new receptacle and ballast added, and the device again sent below.

Figure 5:
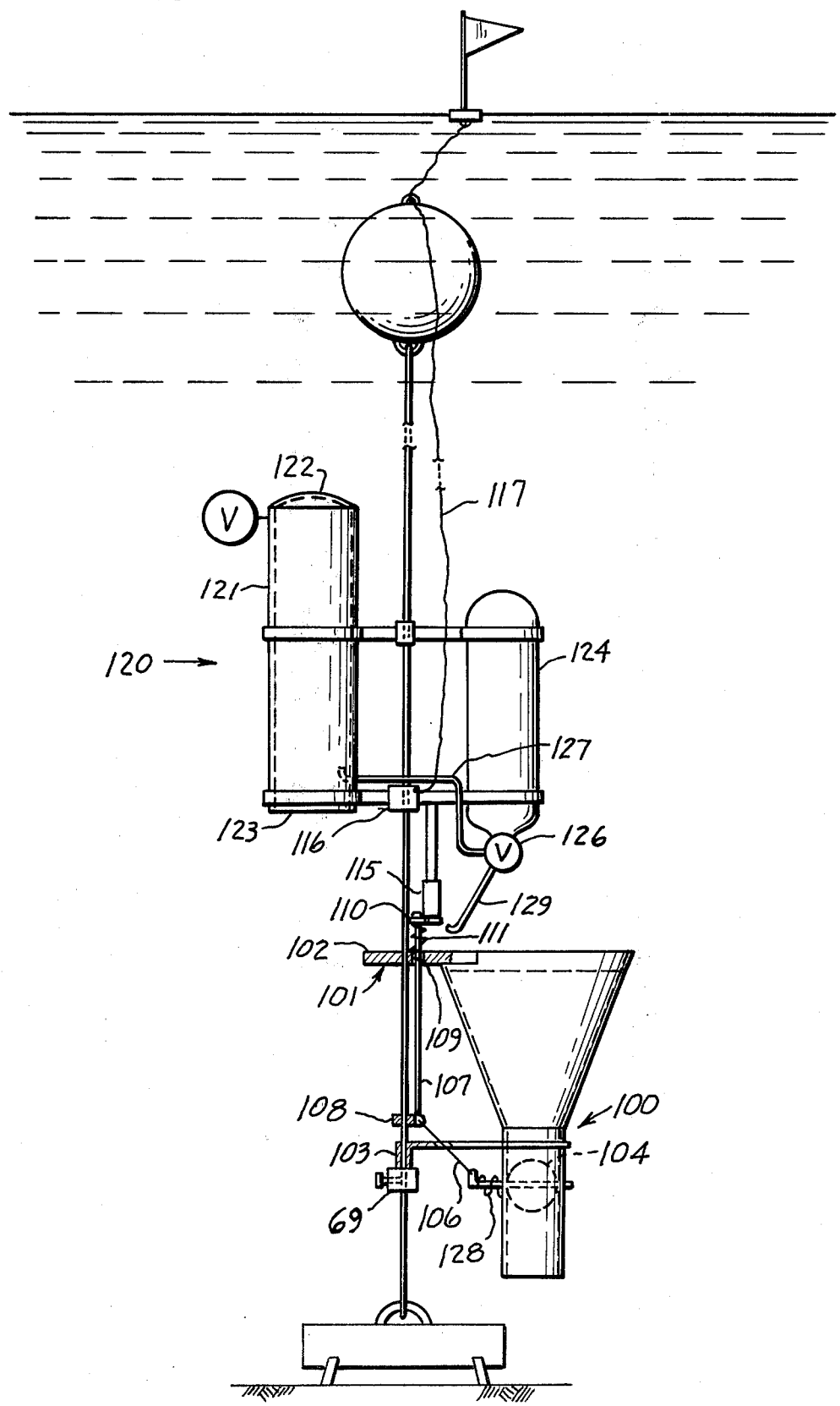
FIG. 5 shows the presently-preferred embodiment of the invention.

FIG. 5 shows two other techniques for recovering the receptacle. Receptacle 100 is the same in all details as that shown in FIGS. 1-4 and the details will not be repeated here. Guide means 101 comprises brackets 102, 103 which slidably fit around the cable and support the receptacle. Valve 104 is biased closed by coil spring 128 as in FIGS. 1-4, but held open by spring 111 which can overpower it and hold the valve open. This includes a flexible cord or cable 106, and a pull rod 107, which rod is attached to a slidable sleeve 108 and passes through an aperture 109 in bracket 102. A striker head 110 is adapted to be abutted against to depress rod 107 and enable the valve to be held closed by its bias spring, as will later be described.

Attachment means 115 comprises a magnet slidably engaged to the cable by a sleeve 116. It is attractive to the magnetizable material of bracket 102.

One means for recovery of the receptacle comprises a flexible line 117 attached to means 115. Buoyancy means can be dispensed with by providing only the line and means 115, and the diver can pull the receptacle and guide means to the surface.

Instead, buoyancy means 120 can be provided which is inherently negatively buoyant so that it will fall down the cable to the receptacle, and permit attachment means 115 to become attached to bracket 102. Buoyancy means 120 comprises an inverted cylinder sometimes called an "inverted shell") 121 with a closed top 122 and an open bottom 123. It also includes a tank 124 containing compressed gas, such as a scuba tank with compressed air. A valve 126 closes the tank and leads to an air line 127 which discharges into cylinder 121. A valve operator 129 is disposed where it can make contact with bracket 102 to open the valve. When water is purged from cylinder 121, sufficient positive buoyancy is developed that the guide means and receptacle, when attached by the magnet, will rise to the lesser depth where the diver can reach it. In this embodiment, ballast is not sacrificed.

In FIGS. 1-4, the assembly is inherently positive, but made negative by discharge of ballast. In FIG. 5, the assembly is inherently negative, but made positive by purging a cylinder, in effect purging water ballast from cylinder 121, but no weight is sacrificed. If the line is used, no buoyancy means is needed.

Either with the use only of the line, or with the buoyancy means without the line, when the collector is to be recovered, the magnet is sent down. It bears against the head of the rod and pushes it down so the bias spring 128 on the valve is able to close the valve. The magnet then attaches itself to bracket 102 with sufficient force that an upward pull on the line, or by the buoyancy means, will raise the guide means and the collector, and hold rod 105 down against the upward force of spring 111. If preferred, latch release means could be used for holding the valve open and releasing it on contact.

If the buoyancy means is also used, it travels with the magnet, and its actuator 129 (sometimes called an "operator") strikes the bracket 102 before the magnet arrives at the bracket. This starts the air purging, but it takes time, and does not prevent or impede the magnet from attaching to the bracket. Then the assembly rises. At the upper limit of travel, the receptacle can be removed and replaced. The valve of the new receptacle will be cocked open, and the guide means and new receptacle will be down. The buoyancy means can be returned to the boat. The sleeves on the buoyancy means may be formed as buckled rings to enable said means readily to be put onto and taken off of the cable. The buoyancy means herein is sometimes referred to as a "lift body."

This specification shows a sediment collector as an example of a retrievable article that is attached to the guide means for recovery. Obviously other types of articles can similarly be attached to the guide means, so that while the retrieval of a sediment collector is the presently-preferred usage of this invention, this example is not a limitation on the generality of the invention as to its application to bring other types of articles to the surface.

It will be understood that the embodiments of the invention illustrated and described herein are given by way of illustration and not of limitation, and that modifications or equivalents or alternatives within the scope of the invention may suggest themselves to those skilled in the art.

I claim:

1. Apparatus adapted to follow an upright cable beneath the surface of a body of water to a first depth, and later to rise to a lesser second depth, said apparatus comprising:

guide means adapted to embrace and slide along said cable;

a retrievable article mounted to said guide means for movement therewith, the combination of said guide means and article having a negative buoyancy so as to sink;

stop means, the depth of which is adjustable, and which can be rigidly attached to said cable to determine said first depth, said stop means restraining said article at said first depth;

buoyancy means adapted to slide along said cable comprising a body having a floodable cavity, said body when the cavity is flooded with water having an inherently negative buoyance, and having positive buoyancy when filled with gas;

attachment means comprising a magnet carried by said buoyancy means so disposed and arranged as to abut against and attach to said guide means when said buoyancy means sinks to the depth of said guide means;

gas supply means carried by said buoyancy means comprising a compressed gas tank connected to said cavity;

gas valve means carried by said buoyancy means connected to said gas supply means to retain gas in said gas supply means until the gas valve means is opened, said gas valve means comprising an operator which is movable and so disposed and arranged relative to said guide means as to open said gas valve means by abutment force when said attachment means is magnetically attached to said guide means, whereby to release gas from said gas supply means to expel water from said cavity, the resulting positive buoyancy of said buoyancy means being adequate to cause the combination of article, buoyancy means, attachment means, guide means, gas supply means, and gas valve means to rise to said second depth.

2. Apparatus according to claim 1 in which said article is a sediment-collecting receptacle with a closed bottom and an open top, and in which a receptacle valve is placed in said open top; and which includes means which closes said receptacle when said gas valve means is released.

3. Apparatus according to claim 2 in which said receptacle valve comprises a pivoted plate which is spring-biased to a closed position, and is held open until released to close when the gas valve means is opened.

4. Apparatus according to claim 1 in which said buoyancy means comprises an inverted shell having a lower opening.

5. Apparatus according to claim 2 in which said buoyancy means comprises an inverted shell having a lower opening.

6. Apparatus according to claim 3 in which said buoyancy means comprises an inverted shell having a lower opening.

* * * * *